United States Patent
Yabe et al.

(10) Patent No.: US 12,194,650 B2
(45) Date of Patent: Jan. 14, 2025

(54) METHOD FOR VIBRATING HANDPIECE-TYPE HIGH-FREQUENCY VIBRATION APPARATUS

(71) Applicant: MICRON MACHINERY CO., LTD., Yamagata (JP)

(72) Inventors: Jinzo Yabe, Kawasaki (JP); Mohee Sagae, Yamagata (JP); Satoshi Kobayashi, Yamagata (JP); Yoshihiro Minagawa, Yamagata (JP)

(73) Assignee: Micron Machinery Co., Ltd., Yamagata (JP)

( * ) Notice: Subject to any disclaimer, the term of this patent is extended or adjusted under 35 U.S.C. 154(b) by 266 days.

(21) Appl. No.: 17/613,320

(22) PCT Filed: Apr. 22, 2020

(86) PCT No.: PCT/JP2020/017410
§ 371 (c)(1),
(2) Date: Nov. 22, 2021

(87) PCT Pub. No.: WO2021/019852
PCT Pub. Date: Feb. 4, 2021

(65) Prior Publication Data
US 2022/0227017 A1 Jul. 21, 2022

(30) Foreign Application Priority Data
Jul. 26, 2019 (JP) .................. 2019-137699

(51) Int. Cl.
*B26D 7/08* (2006.01)
*B06B 1/02* (2006.01)
(Continued)

(52) U.S. Cl.
CPC ............ *B26D 7/086* (2013.01); *B06B 1/0215* (2013.01); *A61B 17/320068* (2013.01);
(Continued)

(58) Field of Classification Search
CPC ..... B26D 7/086; B06B 1/0215; B06B 1/0269; B06B 1/0276; B06B 1/0284;
(Continued)

(56) References Cited

U.S. PATENT DOCUMENTS

| 5,026,387 A | 6/1991 | Thomas |
| 6,577,042 B2 | 6/2003 | Lee et al. |

(Continued)

FOREIGN PATENT DOCUMENTS

| EP | 1 199 048 A2 | 4/2002 |
| JP | H02-116359 A | 5/1990 |

(Continued)

OTHER PUBLICATIONS

The extended European Search Report dated Nov. 22, 2022 issued in the corresponding EP Patent Application No. 20848115.0.

*Primary Examiner* — Phong H Nguyen
(74) *Attorney, Agent, or Firm* — Carrier, Shende & Associates P.C.; Joseph P. Carrier; Fulchand P. Shende

(57) ABSTRACT

The handpiece-type high-frequency vibration apparatus includes a roughly cylindrical housing 10 configuring a handpiece, a holding member 11, a tool 12, a controller 20 and an excitation device 21. In a non-contact state before the tool 12 is brought into contact with an object, the controller 20 drives the excitation device 21 so as to vibrate the tool 12 at an added frequency fp for which a predetermined frequency fs is added to a first resonance frequency fr1 of the tool 12. In a cutting state where the tool 12 is in contact with the object by a load that enables cutting of the object by the tool 12, the controller 20 controls drive of the excitation device 21 such that a third resonance frequency fr3 of the tool 12 increases and coincides with the added frequency fp, and increases a vibration frequency of the tool 12.

6 Claims, 2 Drawing Sheets

(51) Int. Cl.
*A61B 17/32* (2006.01)
*B24B 1/04* (2006.01)

(52) U.S. Cl.
CPC ....... *B06B 2201/55* (2013.01); *B06B 2201/76* (2013.01); *B24B 1/04* (2013.01)

(58) Field of Classification Search
CPC ............ B06B 2201/55; B06B 2201/76; A61B 17/320068; A61B 17/320074; A61B 17/320082; B24B 1/04
See application file for complete search history.

(56) References Cited

U.S. PATENT DOCUMENTS

| | | |
|---|---|---|
| 10,730,158 B2 | 8/2020 | Ketelaer |
| 2012/0123458 A1 | 5/2012 | Giordano et al. |
| 2015/0073357 A1 | 3/2015 | Bagwell et al. |
| 2017/0143369 A1* | 5/2017 | Downey ................ A61B 17/32 |
| 2018/0280073 A1* | 10/2018 | Sanai ....................... A61N 7/02 |
| 2020/0214795 A1 | 7/2020 | Sagae et al. |

FOREIGN PATENT DOCUMENTS

| | | |
|---|---|---|
| JP | H03-60773 A | 3/1991 |
| JP | 2002-035002 A | 2/2002 |
| JP | 2002-514958 A | 5/2002 |
| JP | 2010-042123 A | 2/2010 |
| JP | 2018-526231 A | 9/2018 |
| JP | 2019-088452 A | 6/2019 |
| WO | 91/13591 A1 | 9/1991 |
| WO | 2010/017149 A1 | 2/2010 |

* cited by examiner

METHOD FOR VIBRATING HANDPIECE-TYPE HIGH-FREQUENCY VIBRATION APPARATUS

TECHNICAL FIELD

The present invention relates to a method for vibrating a handpiece-type high-frequency vibration apparatus which performs cutting using a tool attached to a distal end portion.

BACKGROUND ART

A handpiece-type high-frequency vibration apparatus which comprises a handpiece including a vibrating body (vibrator) that ultrasonically vibrates, and cuts an object using a tool (processing unit) attached to a distal end portion is known (for example, Patent Literature 1).

In the handpiece-type high-frequency vibration apparatus described in Patent Literature 1, an ultrasonic vibration transmission member for transmitting vibrations at the vibrating body to the tool is provided, and the ultrasonic vibration transmission member is fixedly connected to the vibrating body in an undetachable state.

When cutting is performed with the handpiece-type high-frequency vibration apparatus described in Patent Literature 1, since cutting easiness and cutting time vary depending on a frequency of the tool, the frequency of the tool is generally tuned to a resonance frequency of the tool.

CITATION LIST

Patent Literature

Patent Literature 1: Japanese Patent Laid-Open No. 2002-035002

SUMMARY OF INVENTION

Technical Problem

However, in a case where the frequency of the tool is tuned to the resonance frequency of the tool, there is a problem in that heat generated by the tool also becomes high.

The present invention is implemented in consideration of the point and has an object to provide a method for vibrating a handpiece-type high-frequency vibration apparatus, which facilitates cutting while suppressing heat increase in a tool.

Solution to Problem

A method for vibrating a handpiece-type high-frequency vibration apparatus of the present invention is the method for vibrating a handpiece-type high-frequency vibration apparatus which includes a handpiece including a vibrating body that ultrasonically vibrates, and which is capable of attaching two or more kinds of tools to a distal end portion of the handpiece and vibrates the tool by the vibrating body, the method comprising: a vibrating step of vibrating the tool, in a non-contact state where the tool is not in contact with an object, at an added frequency in which a predetermined frequency is added to a resonance frequency of the tool in the non-contact state; and a cutting step of driving the vibrating body, in a cutting state of cutting the object by the tool, such that the resonance frequency of the tool in the cutting state increases and approaches the added frequency.

According to the present invention, since the frequency of the tool is tuned to the added frequency for which the predetermined frequency is added to the resonance frequency in the non-contact state before the tool cuts the object, compared to the apparatus for which the frequency of the tool is the resonance frequency, cutting energy becomes low and heat generation of the tool in the non-contact state can be suppressed.

Further, since the vibrating body is driven such that the resonance frequency of the tool increases and approaches the added frequency in the cutting state of cutting the object by the tool, cutting is facilitated.

In addition, it is preferable that the predetermined frequency be variable according to the tool.

According to the configuration, the tool can be vibrated at an appropriate frequency according to the tool.

Further, it is preferable that the predetermined frequency be selectable.

According to the configuration, the frequency of the tool can be set by an operator. Thus, for example, the operator with strong force of pressing the tool to the object when cutting makes the predetermined frequency higher than a threshold and the operator with weak force of pressing the tool to the object when cutting makes the predetermined frequency lower than the threshold, so that the appropriate frequency for facilitating cutting according to a type of the operator can be attained.

DESCRIPTION OF EMBODIMENT

Hereinafter, the embodiment of the present invention will be described with reference to the drawings.

Figure 1:
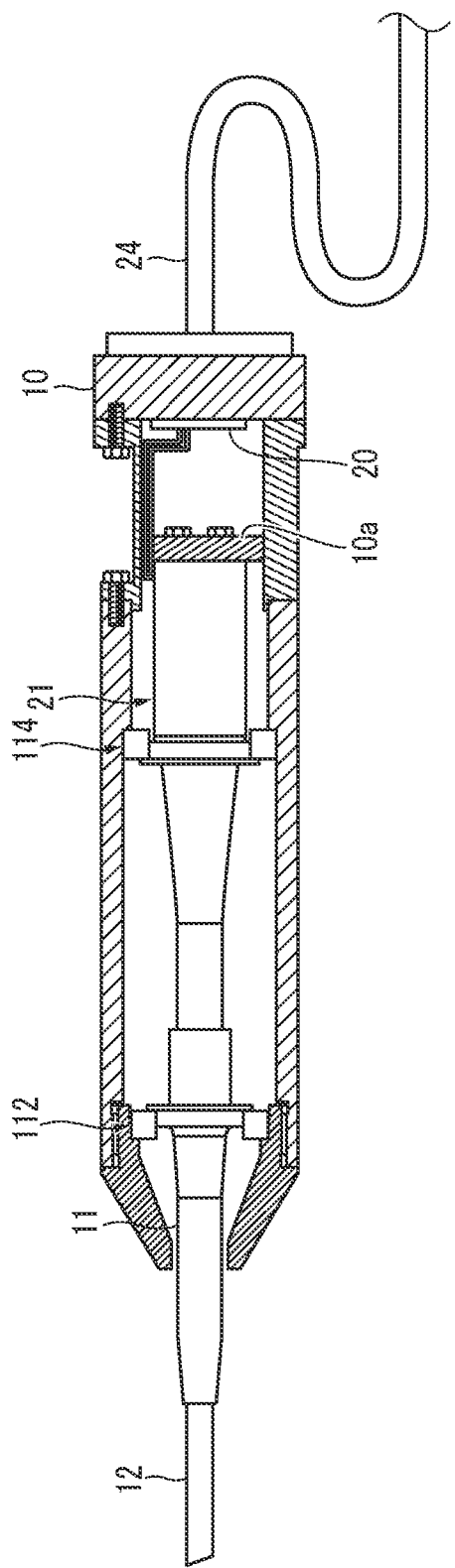
FIG. 1 is an explanatory diagram relating to a configuration of a handpiece-type high-frequency vibration apparatus as one embodiment of the present invention.

As illustrated in FIG. 1, a handpiece-type high-frequency vibration apparatus as one embodiment of the present invention comprises a roughly cylindrical housing 10 configuring a handpiece, a holding member 11, a tool 12, a controller 20 and an excitation device 21.

The housing 10 is designed in a size to be held in one hand by an ordinary person. The handpiece of a high-frequency vibration-type cutting device is configured by components such as the housing 10 and the holding member 11 at least partially arranged in the internal space, and kinds and specifications of the components may be appropriately selected from a viewpoint of reducing weight of the handpiece for handling convenience.

The holding member 11 is attached to the excitation device 21 at the rear end portion, and is supported freely movably in an axial direction to the housing 10 via support portions 112 and 114 fixed to an inner side wall of the housing 10. The holding member 11 has a function as a horn which increases amplitude. The tool 12 is freely detachably attached to a distal end portion of the holding member 11.

A length of the tool 12 in a direction perpendicular to the axial direction of the holding member 11 is 30-150 [mm]. Examples of the kind of the tool 12 are a curette, a chisel, a surgical knife, a file, a long type and a short type. In addition, as a shape of the tool 12, an arbitrary shape such as a blade with a straight or circular arcuate distal end, a roughly columnar shape, a spoon shape, or a bent or curved rod shape is adopted.

The excitation device 21 is attached to an attaching portion 10a of the housing 10, is configured by a piezoelectric element arranged in the internal space of the housing 10, and vibrates or reciprocatingly drives the holding member 11 in the axial direction. Electric power is supplied to the excitation device 21 via a cable 24 attached to the rear end portion of the housing 10 and the controller 20 and a conducting wire arranged in the internal space of the housing 10.

Since the excitation device 21 and the holding member 11 are arranged such that respective axes are in common and separated in relation to the respective axial directions, compared to a case where the axes are separated in parallel or arranged in non-parallel, an occupancy space of the excitation device 21 and the holding member 11 in the internal space of the housing 10, and eventually the housing 10, can be made compact in relation to the direction perpendicular to the axes. Thus, the high-frequency vibration-type cutting device can be configured as the handpiece for which holding comfortableness and operability are improved.

Since force of the excitation device 21 is directly transmitted to the holding member 11 without use of a transmission mechanism, need of lubricant such as grease generally used for the transmission mechanism is eliminated Thus, in the case where the high-frequency vibration-type cutting device as a medical appliance is sterilized by high-pressure steam, a situation where contamination of the medical appliance resulting from presence of the lubricant occurs is avoided.

The controller 20 controls an operation of the excitation device 21. A microcomputer or a processor configuring the controller 20 is arranged in the internal space of the housing 10 together with a substrate on which the microcomputer or the processor is mounted. The controller 20 performs control so that a vibration frequency f2 in the axial direction of the tool 12 via the holding member 11 by the excitation device 21 is included in a range of 20-60 [kHz]. It is more preferable that the control be performed to be f2=25-45 [kHz].

According to the handpiece-type high-frequency vibration apparatus of the configuration described above, by the holding member 11 being reciprocatingly driven in the axial direction, the object is cut by the tool 12 provided on the distal end portion of the holding member 11.

Effects

In the case of cutting the object using the handpiece-type high-frequency vibration apparatus, an operator who performs cutting (surgery) attaches the tool 12 to the distal end portion of the holding member 11. Then, the operator vibrates the holding member 11 (the tool 12) in the axial direction before cutting tissue, a bone in an ear, for example, of a patient as the object by the tool 12 (a non-contact state).

The controller 20 detects a first resonance frequency fr1 of the tool 12 in the non-contact state by a detector (not illustrated). Then, the controller 20 drives the excitation device 21 so as to vibrate the tool 12 at an added frequency fp for which a predetermined frequency fs (to be described later in detail) is added to the first resonance frequency fr1 (energizes a pulse current corresponding to the added frequency fp to the excitation device 21) (a vibrating step).

Figure 2:
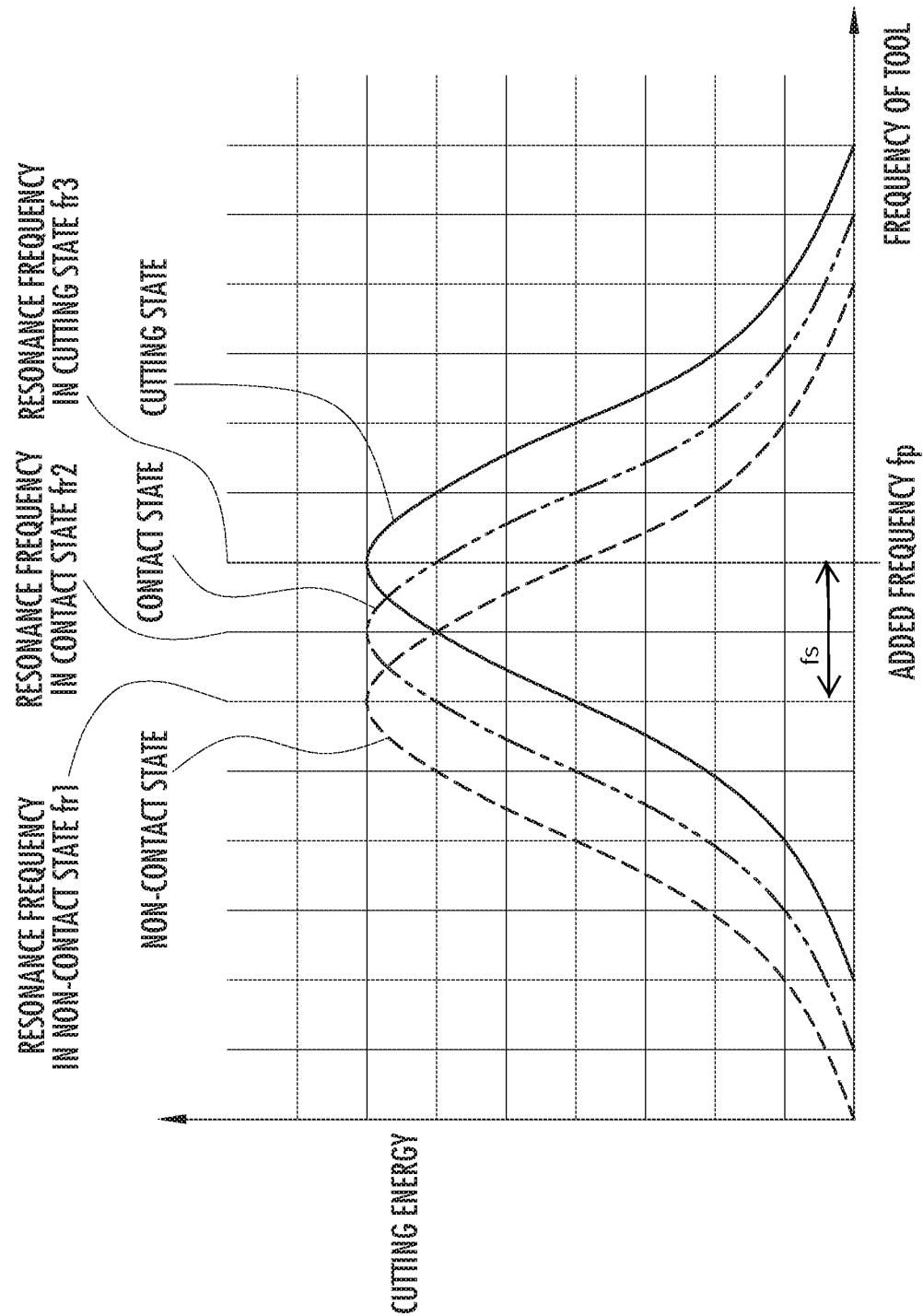
FIG. 2 is a graph illustrating cutting energy according to a frequency of a tool in a non-contact state, a contact state and a cutting state.

Thus, as illustrated by a dotted line in FIG. 2, since the tool 12 is vibrated at the added frequency fp higher than the first resonance frequency fr1 in the non-contact state, in the case where the tool 12 is vibrated at the first resonance frequency fr1, a difference from a resonance frequency is generated, so that vibrating energy becomes low and heat quantity generated by the tool 12 can be reduced. Thus, in the case where the tool 12 is brought into contact with biological tissues (the biological tissues in the ear) around the object, deterioration or damage of the biological tissues is suppressed.

When the tool 12 is brought into contact with the object (a contact state), as a load applied to the tool 12 increases, a second resonance frequency fr2 of the tool 12 in the contact state increases and approaches the added frequency fp. That is, since the difference from the resonance frequency of the tool 12 is reduced, the vibrating energy increases.

In a cutting state where the tool 12 is in contact with the object by the load that enables cutting of the object by the tool 12, the controller 20 controls drive of the excitation device 21 such that a third resonance frequency fr3 of the tool 12 in the cutting state increases and coincides with the added frequency fp (a cutting step). Also in the cutting state, the tool 12 is vibrated at the added frequency fp. In the present embodiment, for the predetermined frequency fs, a frequency that enables the third resonance frequency fr3 to coincide with the added frequency fp is set. Without being limited to the coincidence, the third resonance frequency fr3 may be made to approach the added frequency fp.

Thus, as illustrated by a solid line in FIG. 2, in the cutting state, since the tool 12 can be vibrated at the third resonance frequency fr3 (added frequency fp), the object can be cut with high cutting energy without causing vibration attenuation by the load to the tool 12 and cutting efficiency is high.

Note that the predetermined frequency fs may be settable by the operator. For example, the operator with strong force of pressing the tool 12 to the object when cutting makes the predetermined frequency fs higher than a threshold, and the operator with weak force of pressing the tool 12 to the object when cutting makes the predetermined frequency fs lower than the threshold. Thus, the appropriate predetermined frequency according to a type of the operator can be attained.

In the present embodiment, between the contact state and the cutting state, the drive of the excitation device 21 is controlled so as to increase the resonance frequency of the tool 12 according to increase of the load of the tool 12 in contact with the object. That is, the cutting energy increases according to the increase of the force (the force of pressing the tool 12 to the object) applied by the operator.

Conventionally, when a bone curette is used, for instance, as the tool 12, a cutting amount of the bone (object) is controlled by force adjustment of the operator. In the present embodiment, since the cutting energy (oscillation power) increases according to the force adjustment applied by the operator, the force to be applied can be reduced while utilizing a past operator sensation, and delicate work can be supported without stress.

In addition, in the case of cutting the object (the bone) in water while securing an operating field using an endoscope, when the cutting energy of the tool 12 is high, since the water around the tool 12 is largely shaken and bone dust and soft tissues are shaken by a water current, a visual field of the endoscope is obstructed, however, according to the present embodiment, workability is improved since the cutting energy is suppressed until right before cutting the bone.

The ideal embodiment of the present invention has been described above, however, the present invention is not limited by such an embodiment, and appropriate modifications are possible without departing from the gist of the present invention.

For example, while the first resonance frequency fr1 of the tool 12 in the non-contact state is detected by the detector in the embodiment described above, the first resonance frequency fr1 of each of the two or more kinds of tools 12 may be stored in a memory (not illustrated) beforehand and the controller 20 may read the first resonance frequency fr1 from the memory according to the kind of the tool 12 attached to the distal end portion of the holding member 11.

In this case, the handpiece-type high-frequency vibration apparatus further comprises an input interface for making the operator input the kind of the tool 12. The input interface is configured by a keyboard, touch panel-type button or an operation button or the like, for example.

REFERENCE SIGNS LIST

10 . . . Housing, 11 . . . Holding member, 12 . . . Tool, 20 . . . Controller, 21 . . . Excitation device

The invention claimed is:

1. A method for vibrating a handpiece-type high-frequency vibration apparatus which includes a handpiece including a vibrating body that ultrasonically vibrates, and which is configured to attach two or more kinds of tools to a distal end portion of the handpiece and vibrates an attached one of the tools by the vibrating body, the method comprising:
   a vibrating step of driving the vibrating body so as to vibrate the tool in a non-contact state where the tool is not in contact with an object; and
   a cutting step of driving the vibrating body so as to vibrate the tool in a cutting state of cutting the object by the tool,
   wherein in both the vibrating step and the cutting step the tool is vibrated at a fixed predetermined frequency that exceeds a resonance frequency of the tool in the non-contact state, and
   wherein a cutting energy of the tool as vibrated at the fixed predetermined frequency in the non-contact state is less than a cutting energy of the tool as vibrated at the fixed predetermined frequency in the cutting state.

2. The method for vibrating the handpiece-type high-frequency vibration apparatus according to claim 1,
   wherein the resonance frequency of the tool in the cutting state is variable according to the kind of tool.

3. The method for vibrating the handpiece-type high-frequency vibration apparatus according to claim 1,
   wherein the fixed predetermined frequency corresponds to a sum of the resonance frequency of the tool in the non-contact state plus a predetermined frequency, and
   wherein the predetermined frequency is selectable by an operator.

4. A handpiece-type high-frequency vibration apparatus which includes a handpiece including a vibrating body that ultrasonically vibrates and which is configured to attach two or more kinds of tools to a distal end portion of the handpiece and vibrates an attached one of the tools by the vibrating body, and a controller which controls an operation of the vibrating body, wherein: the controller controls the operation of the vibrating body so as to vibrate the tool, in a non-contact state where the tool is not in contact with an object and in a cutting state of cutting the object by the tool, at a fixed predetermined frequency that exceeds a resonance frequency of the tool in a non-contact state, and
   wherein a cutting energy of the tool as vibrated at the fixed predetermined frequency in the non-contact state is less than a cutting energy of the tool as vibrated at the fixed predetermined frequency in the cutting state.

5. The handpiece-type high-frequency vibration apparatus according to claim 4, wherein the resonance frequency of the tool in the cutting state is variable according to the kind of tool.

6. The handpiece-type high-frequency vibration apparatus according to claim 4, wherein the fixed predetermined frequency corresponds to a sum of the resonance frequency of the tool in the non-contact state plus a predetermined frequency, and
   wherein the predetermined frequency is selectable by an operator.

* * * * *